United States Patent
Schmitt et al.

(10) Patent No.: US 7,071,351 B2
(45) Date of Patent: Jul. 4, 2006

(54) SYNTHESIS OF ALKYLAMINOALKYL (METH)ACRYLATE BY TRANSESTERIFICATION

(75) Inventors: Bardo Schmitt, Mainz (DE); Joachim Knebel, Alsbach-Haehnlein (DE); Maik Caspari, Alsbach-Haehnlein (DE)

(73) Assignee: Roehm GmbH & Co. KG, Darmstadt (DE)

( * ) Notice: Subject to any disclaimer, the term of this patent is extended or adjusted under 35 U.S.C. 154(b) by 102 days.

(21) Appl. No.: 10/486,351

(22) PCT Filed: Aug. 16, 2002

(86) PCT No.: PCT/EP02/09197

§ 371 (c)(1),
(2), (4) Date: Feb. 27, 2004

(87) PCT Pub. No.: WO03/022796

PCT Pub. Date: Mar. 20, 2003

(65) Prior Publication Data

US 2004/0249191 A1 Dec. 9, 2004

(30) Foreign Application Priority Data

Sep. 13, 2001 (DE) ................................ 101 45 228

(51) Int. Cl.
*C07C 67/03* (2006.01)

(52) U.S. Cl. ...................................................... 560/217

(58) Field of Classification Search ................. 560/205, 560/217, 129, 215
See application file for complete search history.

(56) References Cited

FOREIGN PATENT DOCUMENTS

| EP | 837 049 | 4/1998 |
|---|---|---|
| EP | 1 078 913 | 2/2001 |
| EP | 1 201 640 | 5/2002 |
| FR | 2 747 675 | 10/1997 |
| JP | 62230755 | * 10/1987 |
| JP | 02-017155 | 1/1990 |
| JP | 02-059546 | 2/1990 |
| JP | 03-181449 | 8/1991 |
| JP | 03181449 | * 8/1991 |

* cited by examiner

*Primary Examiner*—Johann Richter
*Assistant Examiner*—Karl Puttlitz
(74) *Attorney, Agent, or Firm*—Oblon, Spivak, McClelland, Maier & Neustadt, P.C.

(57) ABSTRACT

The invention relates to a method for transesterifying methyl methacrylate involving catalysis, particularly zirconium acetylacetonate catalysis. The obtained esters of formula (I) are characterized by having an extremely low content of cross-linking agents.

3 Claims, No Drawings

SYNTHESIS OF ALKYLAMINOALKYL (METH)ACRYLATE BY TRANSESTERIFICATION

BACKGROUND OF THE INVENTION

1. Field of the Invention

The invention relates to a process for transesterifying esters of unsaturated carboxylic acids with reactive alcohols and with a catalyst for these processes.

2. Description of the Background

It is known to prepare carboxylic esters by transesterification.

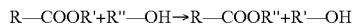

R generally represents an aliphatic or aromatic group, R' may be for example methyl or ethyl, and R" is a group which may contain more carbon atoms than R'. R' and R" may be selected so that the alcohol formed is more volatile than the ester. The use of a catalyst speeds equilibration.

The present invention relates to the synthesis of t-butylaminoethyl methacrylate by transesterification of t-butylaminoethanol with methyl methacrylate (MMA). The transesterification is known per se. JP 062717517 and JP 06256271 describe the transesterification of methyl methacrylate with t-butylaminoethanol under $K_2CO_3$ catalysis. Disadvantages here are the relatively long reaction time (5 hours) and the appearance of byproducts (91% purity), so that the product has to be purified by distillation.

JP 62185059 and JP 62175448 describe the synthesis of diethylaminoethyl methacrylates in the presence of $K_2CO_3$, $Rb_2CO_3$, $Cs_2CO_3$. The purity achieved is above 95%, but the reaction still takes 5 hours.

JP 62242652 describes the use of $KHCO_3$ as a catalyst. Disadvantages here are that the reaction likewise takes 5 hours and a distillation is needed to purify the crude product. Generally, alkaline catalysts lead increasingly to double bond adducts, especially in the presence of amines.

EP 298867 describes catalysis by means of titanium (IV) alkoxide. It is to be noted that this method too requires a distillative workup to obtain a purity >98%. Titanium catalysts are also $H_2O$ sensitive, which makes the synthesis more costly and more inconvenient to perform.

JP 62230755 describes $K_3PO_4$ catalysis. The disadvantage is again the reaction time of 5 hours for a conversion of 83.5%.

JP 56104851 utilizes dibutyltin oxide as a catalyst. This catalyst has the disadvantage that 8 hours are needed for a conversion above 95%.

Alkali metal oxides are disclosed in FR 1568382 and GB 1174148. The disadvantage here is that conversions are <95% and the yield is only slightly above 80%.

EP 160427 (Allied Colloids) describes the transesterification of methacrylates in the presence of an alcohol and/or in the presence of a mixture of alkoxides of that alcohol and/or of methanol with Ca, Mg or Ba, Ti and Zr or Al. The catalyst is recyclable.

The prescription is to transesterify dimethylaminoethanol (DMEA) with MMA to form DMAEA (dimethylaminoethyl methacrylate). The disadvantage here is that the alcohol first has to be converted into the metal alkoxide (which is costly and inconvenient to do) in order then to be used in a large amount in the synthesis (DMEA ligand:MMA=3:4).

EP 118 639 (Allied Colloids) describes a transesterification process catalyzed by metal alkoxides of metals Ti, Al, Zr, Ca or Mg.

U.S. Pat. No. 2,138,763 describes the transesterification of methyl methacrylate with different amino alcohols in the presence of sodium methoxide.

A reaction has to be carried out in the absence of water and reactive alcohols. The best results are achieved with calcium or magnesium as metal component. Nothing is said about the by-product spectrum.

SUMMARY OF THE INVENTION

It is an object of the present invention to provide a further process for transesterifying unsaturated carboxylic esters. The catalyst shall be simple to prepare and be easy to separate off.

The invention describes the process for transesterification of reactive alcohols with methyl methacrylate. Reactive alcohols are alcohols having one or more functional groups, for example hydroxyl groups, amino groups, substituted amino groups, thiol groups, epoxy groups.

The advantage of the inventive achievement, which consists in catalyzing the transesterification by means of zirconium acetylacetonate, is a methacrylic ester having a lower crosslinker content. The yield based on the raw materials used is higher, fewer by-products are formed.

DETAILED DESCRIPTION OF THE PREFERRED EMBODIMENTS

This object and other objects not expressly mentioned but readily derivable or discernible from the above context are achieved by a process of claim 1. Advantageous modifications of the inventive process are protected in subclaims appendant to claim 1.

Reaction Equation

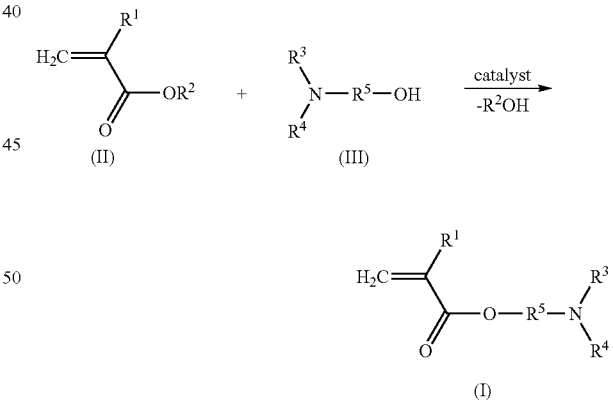

$R^1$=H, $CH_3$ $R^2$=H, $CH_3$, $CH_2$—$CH_3$ $R^3$=H, $CH_3$, $CH_2$—$CH_3$
propyl, isopropyl,
butyl, isobutyl, t-butyl $R^4$=$CH_3$, $CH_2$—$CH_3$
propyl, isopropyl
butyl, isobutyl, t-butyl

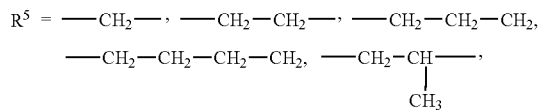

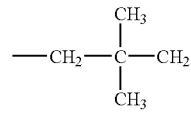

Not only zirconium acetylacetonate may be used as a catalyst but also other 1,3-diketonates of zirconium, for example 1,3-diphenylpropane-1,3-dione.

EXAMPLES

General Experimental Description 117.2 g (1 mol) of 2-(tert-butylamino)ethanol, 500 g (5 mol) of methyl methacrylate (MMA), catalyst (1–2% based on batch, see table) and stabilizer (0.62 g of Irganox 1076/octadecyl 3-(3,5-di-tert-butyl-4-hydroxyphenyl)propionate, 0.012 g of 4-hydroxy-2,2,6,6-tetramethylpiperidinooxyl) are charged to a reaction flask equipped with a column and an automatic columnar head and heated up. The transesterification is carried out at a head temperature of 70° C. by withdrawing the methanol-MMA azeotrope. If the temperature rises, distillate is withdrawn at a reflux ratio of 10:1 up to a temperature of 100° C. Subsequently, excess MMA is distilled off under reduced pressure.

The table shows that the amount of EGDMA is reduced by at least 50% compared with dioctyltin oxide catalysis. Much more significant, however, is the decrease to below 0.1% for the high-boiling crosslinker MtBMAA. The catalyst is easily removed by distillation.

What is claimed is:
1. A transesterification process, comprising:
preparing a compound of formula I:

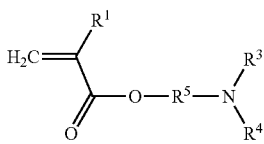

wherein $R^1$ is hydrogen or methyl, $R^3$ is hydrogen, methyl, ethyl, propyl, isopropyl, butyl, isobutyl or t-butyl, $R^4$ is methyl, ethyl, propyl, isopropyl, butyl, isobutyl or t-butyl, and $R^5$ is methylene, ethylene, 1,3-propylene, 1,4-butylene, 2-methyl-ethylene or 2,2-dimethyl-propylene by reacting a compound of formula II

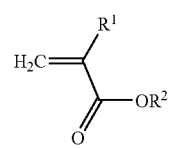

wherein $R^1$ is as defined above and $R^2$ is hydrogen, methyl or ethyl with a compound of formula III

TABLE

| Run No. | Catalyst % based on batch | Alcoholysis Time h | tBAEMA crude ester GC:tBAEMA area % | | | | |
|---|---|---|---|---|---|---|---|
| | | | MMA | tBAE | tBAEMA | EGDMA | MtBMAA |
| 1 (comparison) | dioctyltin oxide 1.5 | 2.5 | 0.56 | 0.75 | 93.30 | 0.02 | 4.23 |
| 2 (comparison) | tetraisopropyl titanate | 6 | 4.38 | 2.06 | 86.09 | 0.02 | 2.02 |
| 3 | zirconium acetylacetonate 2.0 | 2 | 1.22 | 0.04 | 97.38 | 0.01 | 0.08 |
| 4 | zirconium acetylacetonate 1.0 | 2 | 0.26 | 0.04 | 98.39 | <0.01 | 0.06 |
| 5 | zirconium acetylacetonate 0.5 | 2.5 | 1.26 | 0.01 | 97.43 | <0.01 | 0.07 |
| 6 | zirconium acetylacetonate 0.25 | 2.5 | 0.04 | 0.03 | 98.89 | <0.01 | 0.05 |
| 7 | zirconium acetylacetonate 0.10 | 4.25 | 0.41 | 0.04 | 98.41 | <0.01 | 0.06 |

MMA = methyl methacrylate
TBAE = tert-butylaminoethanol
TBAEMA = tert-butylaminoethyl methacrylate
EGDMA = ethylene glycol dimethacrylate
MtBMAA = N,N-(methacryloyloxyethyl)-tert-butylmethacrylamide

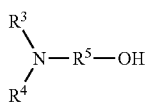
wherein R³, R⁴ and R⁵ are as defined above, in the presence of a catalyst of zirconium acetylacetonate in an amount ranging from 0.1–5% by weight, based on the total weight of the reactants.
2. The process according to claim 1, which is conducted continuously or in a batchwise fashion.
3. The process according to claim 1, wherein the compound of formula III is t-butylaminoethanol.
* * * * *